United States Patent [19]

Haslam et al.

[11] Patent Number: 4,474,753

[45] Date of Patent: Oct. 2, 1984

[54] TOPICAL DRUG DELIVERY SYSTEM UTILIZING THERMOSETTING GELS

[75] Inventors: John L. Haslam; Takeru Higuchi; Arthur R. Mlodozeniec, all of Lawrence, Kans.

[73] Assignee: Merck & Co., Inc., Rahway, N.J.

[21] Appl. No.: 495,321

[22] Filed: May 16, 1983

[51] Int. Cl.$^3$ .................. A61K 31/74; A61K 31/70; A61K 31/135; A61K 31/54; A61K 31/415; A61K 31/435; A61K 31/19; A61K 31/66

[52] U.S. Cl. .................. 424/78; 424/285; 424/85; 424/300; 424/309; 424/94; 424/311; 424/313; 424/114; 424/317; 424/321; 424/116; 424/322; 424/324; 424/177; 424/326; 424/330; 424/180; 424/343; 424/181; 424/209; 424/211; 424/220; 424/221; 424/224; 424/230; 424/238; 424/243; 424/246; 424/248.51; 424/251; 424/253; 424/254; 424/256; 424/258; 424/263; 424/265; 424/267; 424/270; 424/271; 424/273 P; 424/273 R; 424/274; 424/275; 424/283

[58] Field of Search .................. 424/78, 85, 94, 114, 424/116, 177, 180, 181, 209, 211, 220, 221, 224, 230, 238, 243, 246, 248.51, 251, 253, 254, 256, 258, 263, 265, 267, 270, 271, 273 P, 273 R, 274, 275, 283, 285, 300, 309, 311, 313, 317, 321, 322, 324, 326, 330, 343

[56] References Cited

U.S. PATENT DOCUMENTS

| | | | |
|---|---|---|---|
| 2,979,528 | 4/1961 | Lundsted | 260/584 |
| 3,711,604 | 1/1973 | Colodney et al. | 424/78 |
| 3,884,826 | 5/1975 | Phares et al. | 424/78 |
| 4,188,373 | 2/1980 | Krezanoski | 424/177 |

FOREIGN PATENT DOCUMENTS 1072413  7/1976  Canada .

OTHER PUBLICATIONS

Journal of Pharm. & Pharmacology–"Novel Poloxamer & Poloxamine Hydrogels: Swelling & Drug Release", vol. 32, p. 5P (1980) By, A. Saden, A. J. Florence, T. L. Whateley.

Primary Examiner—Douglas W. Robinson
Attorney, Agent, or Firm—Manfred Polk; Michael C. Sudol, Jr.

[57] ABSTRACT

This invention relates to a unique drug delivery system for application to the skin which drug delivery system is a liquid at room temperature, but when administered topically to the skin becomes a semi-solid or gel when warmed by the body.

48 Claims, 1 Drawing Figure

TOPICAL DRUG DELIVERY SYSTEM UTILIZING THERMOSETTING GELS

BACKGROUND OF THE INVENTION

A goal of pharmaceutics is to efficiently deliver a therapeutic drug to the site of action. Over the years, methods have been developed to achieve this goal. We describe here a unique drug delivery system which at room temperature and lower has the property of a liquid but when administered topically to the skin becomes a semi solid or gel when warmed by the body. The advantages of such a system for application to the skin are (1) the drug delivery system can be applied to tender, sensitive skin by a pour on application with no need to rub the area to obtain coverage, and (2) a liquid will flow into crevices and pores providing intimate contact with the skin.

When gelled, the drug delivery system remains in place with a flexible covering to the area of skin on which it is applied. Drugs are delivered to the skin from the gel but these drugs can also be removed by running cool water over the area. Such a drug delivery system will have application especially for burn patients where application and removal of drugs required gentle techniques because of the tender surface to which application is to be made.

A drug delivery system has been described in U.S. Pat. No. 4,188,373 using "Pluronic ®" polyols as the thermally gelling polymer. In this system the concentration of polymer is adjusted to give the desired sol-gel transition temperature, that is the lower the concentration of polymer the higher is the sol-gel transition temperature. However, with the commercially available "Pluronic ®" polymers the ability to obtain a gel of the desired rigidity is limited while maintaining the desired sol-gel transition temperature at physiologically useful temperature ranges near 26°–35° C.

Similarly, a Canadian Pat. No. 1,072,413 which relates to "Pluronic ®" polyols (poloxamer polyols) with gelling temperatures lower than room temperature uses additives to modify the gelling characteristics. Also, in this Canadian patent "Tetronic ®" polymers (poloxamine polyols) are used as additive agents rather than the primary polymeric agent as in the instant case.

SUMMARY OF THE INVENTION

The present invention provides a pharmaceutical vehicle which is useful in delivering pharmacologically active medicaments to the skin of a patient (both animal and human) for topical, dermal and/or transdermal delivery of candidate drugs.

The drug delivery system consists of a clear physiologically acceptable liquid which forms a semi-solid or gel at body temperature. The unique gelling characteristics of the various formulations permit retention of the system at skin interfaces which might otherwise be rapidly depleted of liquid drug delivery systems in areas such as between fingers or toes, in groin areas, under the breasts or arms or on the scalp. The sol-gel transition temperature and rigidity of the gel can be modified by changes in polymer concentration combined with the pH and ionic strength of the solution.

It has been discovered that certain polymers are useful vehicles having the properties set forth above. The polymers are tetra substituted derivatives of ethylene diamine, poloxamine (w=2 in Formula I), propylene diamine (w=3), butylene diamine (w=4), pentylene diamine (w=5) or hexylene diamine (w=6). The substituents are block copolymers of poly(oxypropylene) and poly(oxyethylene) of various chain lengths and ratios x to y in the general formula of the polymer shown below.

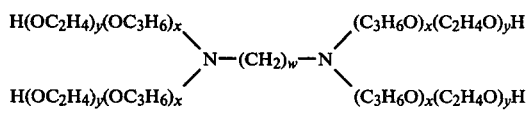

Formula I wherein w is an integer from 2 through 6.

A typical polymer system of our invention would contain a polymer containing approximately 40 to 80% poly(oxyethylene) to approximately 20 to 60% poly(oxypropylene). The total molecular weight of the polymer used in our invention is greater than 7,000 and can go as high as 50,000 but preferably is in the range of 7,000 to 30,000, and x and y are any integers within the above constraints. Preferred polymers are those of the formula above wherein w=2, namely the poloxamine polymers.

The aqueous drug delivery vehicle would contain from 10% to 50% by weight of the entire vehicle of polymer described above. The aqueous drug delivery vehicle would also contain the drug or therapeutic agent in addition to various additives such as acids or bases to adjust the pH of the composition, buffers to maintain the pH, preservatives to control bacterial contamination, other additives to provide the drug solubility and stability and formulation performance with purified water making up the remainder of the drug delivery vehicle.

DETAILED DESCRIPTION OF THE INVENTION

Figure 1:
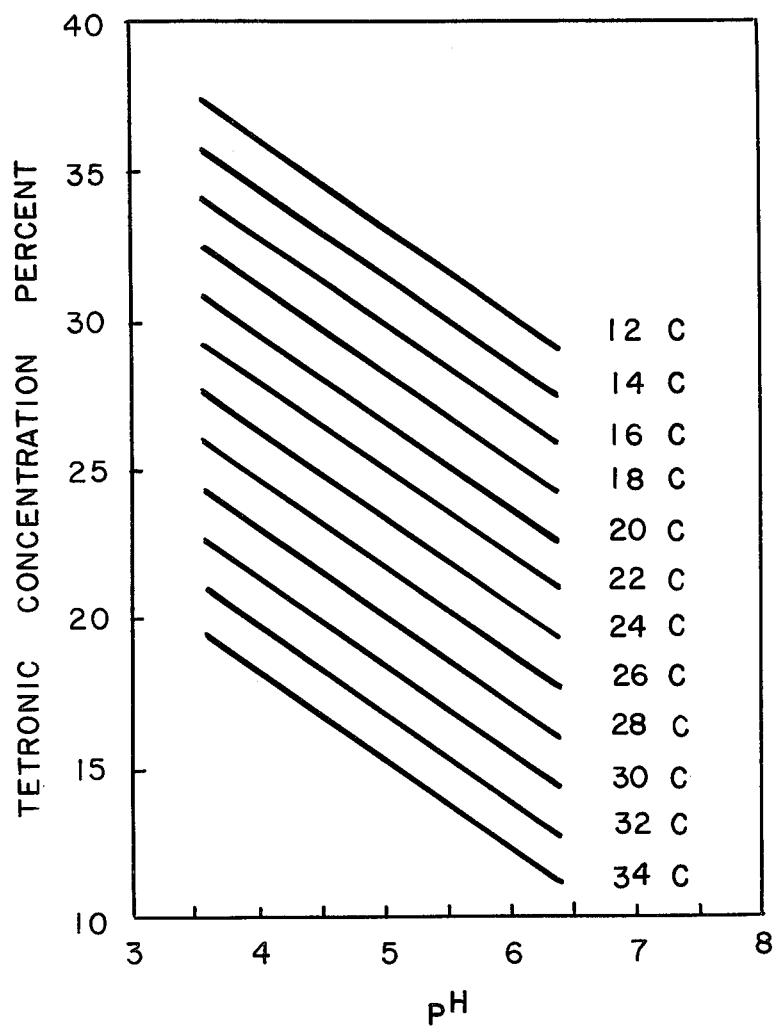

The invention consists of a pharmaceutical composition or drug delivery system which is a clear physiological acceptable solution at room temperature or lower but which forms a semi-solid or gel when warmed to body temperature. The unique feature of this system is that both the gel transition temperature and/or the rigidity of the gel can be modified by adjustment of the pH and/or ionic strength and polymer concentration.

The ability to change the gel-sol transition temperature by pH adjustment is a critical feature of the invention which overcomes many of the disadvantages of previous approaches. Also the gel-sol transition temperature can be modified somewhat by ionic strength adjustment.

An example of a drug delivery vehicle in accordance with this invention consists of an aqueous solution of, for example, a selected tetra substituted ethylene diamine block copolymer of poly(oxyethylene)-poly(oxypropylene) (where w=2 in Formula I) in which the substitution at the nitrogen is to the poly(oxypropylene) block and the polymer consists of about 40–80% as the poly(oxyethylene) unit and about 20–60% as the polypropylene unit and which has a total average molecular weight of 7,000 to 50,000 with a preferred range of 7,000–30,000, and x and y are any integers within the above constraints. Such polymers are included in the polymers sold under the trademark "Tetronic ®" polyols by BASF Wyandotte Corporation.

Other polymers where w=3 to 6 (of Formula I) can be made according to methods known in the art (Block and Graft Copolymerization, Vol. 2 edited by R. J. Ceresa published by John Wiley and Sons, 1976) by using the appropriate initiators such as for example propylenediamine, butylenediamine, pentylenediamine and hexylenediamine.

The preferred polymers are those which form gels at a concentration range of 10 to 50% of the polymer to water.

A good example of a typical polymer used in the drug delivery system of our invention is Tetronic ® 1307 which thermally gels over a concentration range of about 15 to 35% in water with gelling temperatures of about 30° to 10° C. at neutral pH. The gel strength at 35% is much more rigid than the 15% gel. However, with a gel-sol transition temperature of about 10° C. any useful liquid product would have to be refrigerated below this temperature. A useful vehicle can be prepared, however, by modification of both concentration and pH. For example, a 27% Tetronic ® 1307 solution at neutral pH has a sol-gel transition temperature of about 16° C. but at pH 4 (adjusted to such with HCl at 10° C.) the transition temperature is about 25° C. The gel formed under these conditions meets the requirements of a fairly rigid gel which is a liquid at room temperature.

The effect of pH and polymer concentration on gelling temperature for Tetronic ® 1307 is shown in FIG. 1. Thus, for example, at a concentration of polymer to water of 25% the gelling temperature is 19° C. at pH 6 and increases to 26° C. at pH 4.

For administration of the drug delivery system of our invention to the skin, the pH of the system can range from 2 to 9 with the preferred pH range being 4 to 8. The pH, concentration and gelling temperatures will vary for any individual polymer falling within the class covered in this invention and these factors can be determined by those skilled in the art in possession of this concept.

The pH of the drug delivery system is adjusted by adding the appropriate amount of a pharmaceutically acceptable acid or base to obtain the required pH. The acid or base can be any that are known to persons skilled in the art but are preferably hydrochloric acid or sodium hydroxide.

In general, the drug delivery vehicle of the present invention will contain from about 0.01 to about 5% of the medicament or pharmaceutical, from about 10 to about 50% of the polymer and from 90 to about 45% water. In special situations, however, the amounts may be varied to increase or decrease the dosage schedule.

If desired, the drug delivery vehicle may also contain, in addition to the medicament, buffering agents and preservatives, suitable water soluble preservatives which may be employed in the drug deliery vehicle which are sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from 0.001 to 5% by weight and preferably 0.01 and 2%. Suitable water soluble buffering agents are alkali or alkali earth carbonate, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent can be as much as 5% on a weight to weight basis of the total composition.

Any pharmaceutically active material may be delivered in the drug delivery system of this invention. Preferably the drug or pharmaceutical is water soluble although some drugs will show greater solubility in the polymer system than others. Also the drugs may be insoluble and can be suspended in the polymer vehicle.

Another factor which can affect the gelling temperature of the drug delivery vehicle or pharmaceutical composition is the ionic strength and this is done by adding a pharmaceutically acceptable salt, such as sodium chloride, potassium chloride or mixtures thereof or even suitable alkali metal salts such as sodium sulfate and the like. The effect of adding sodium chloride is to decrease the gelling temperature by about 3° C. for a change of 0.2 molar in ionic strength.

Suitable drugs which can be administered by the drug polymer delivery system of the present invention that might be mentioned are antibacterial substances such as beta-lactam antibiotics, such as cefoxitin, n-formamidoyl thienomycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acid and analogs such as norfloxacin and the antimicrobial combination of fludalanine/pentizidone; nitrofurazones, anti-infectives such as iodine, chloramines, benzalkonium chloride, phenol and the like; anti-inflammatories such as cortisone, hydrocortisone, beta-methasone, dexamethasone, fluocortolone, prednisolone, triamcinolone, indomethacin, sulindac, its salts and its corresponding sulfide, and the like; anesthetics such as benzocaine, lidocaine, dibucaine and the like; analgesics such as methyl salicylate, menthol, camphor, methyl nicotinate, triethanolamine salicylate, glycol salicylate and salicylamide and the like; antifungal agents such as tolnaftate, undecylenic acid, salicylic acid, zinc undecylenate and thiabendazole and the like. Also included are antiparasitic compounds such as ivermectin, antiviral effective compounds such as idoxuridine, acyclovir and interferon.

Typically as stated previously, the present liquid drug delivery system would contain from about 0.001 to about 5% of the medicament or pharmaceutical on a weight to weight basis. Thus, from one gram of the liquid conposition which is about 1 ml of solution, one would obtain about 0.1 mg to about 50 mg of medicament or pharmaceutical.

The particular drug used in the pharmaceutical composition of this invention is the type which a patient wuld require for pharmacological treatment of the condition from which said patient is suffering. For example, if the patient is suffering from pain or itch of the skin, the drug of choice would probably be benzocaine.

Included in this invention is the use in this drug delivery device of a diagnostic agent. The diagnostic agents are incorporated into the composition so as to provide visual detection of skin or organic disorders such as in the use of liquid crystals (cholesteryl esters) in the application of diagnostic thermography. The diagnostic agents can be selected from the cholesterol esters such as cholesteryl n-alkyl carbonates, the oleyl carbonate, nonanoate and/or benzoate all in proper proportions to effect liquid crystal response.

Also included in this invention is the use of the drug delivery device or pharmaceutical composition minus the active drug, medicament or diagnostic agent for use as a protective covering for the skin or for lubricating or emollient reasons so as to maintain proper mechanical function of the skin. When used to restore the skin to a flexible and emollient condition the moisture content of the skin is restored to a normalized value, that is a 8–15% w/w of the stratum corneum. All the ratios of components as described above would be satisfactory for this composition. For this use, one would administer the vehicle as needed at the desired pH.

The preparation of the drug delivery systems are described below and the appropriate examples which follow were all carried out according to this procedure. Since the tetronic polymer systems of this invention dissolved better at reduced temperatures, the preferred methods of solubilization are to add the required amount of polymer to the amount of water to be used. Generally, after wetting the polymer by shaking, the mixture is capped and placed in a cold chamber or in a thermostated container at about 0° C. to 10° to dissolve the polymer. The mixture can be stirred or shaken to bring about a more rapid solution of the polymer.

The drug substance and various additives such as buffers, salts and preservatives are then added and dissolved. The final desired pH adjustment can be made by adding the appropriate acids or bases such as hydrochloric acid or sodium hydroxide. Any convenient method can be used to apply the pharmaceutical composition to the skin such as a bottle from which the solution is poured on. A ball roller can be used or a dropper-type application employing a rubber dropper.

EXAMPLES

The following examples are illustrations and are not intended to be restrictive of the scope of the invention. All percentages are given in (w/w)% and all pH measurements are for 10° C.

EXAMPLE 1

The use of the polymer vehicle to deliver norfloxacin, a broad-spectrum antimicrobial compound.

|  | Solution 1 | Solution 2 | Solution 3 |
|---|---|---|---|
| Norfloxacin | 0.1% | 0.1% | 0.1% |
| Tetronic ® 1307 | 22.0% | 27.0% | 32.0% |
| pH adjusted with HCl to 4 |  |  |  |
| sufficient purified water to make | 100% | 100% | 100% |
| gel-sol transition | 30° C. | 26° C. | 21° C. |

All these solutions can be administered as described previously as liquids, however, solution 3 would require cooling to below 21° C. before use.

EXAMPLE 2

| Dexamethasone | 0.05% |
|---|---|
| Tetronic ® 1307 | 30.0% |
| Benzalkonium chloride | 0.02% |
| pH adjusted with HCl to 4 |  |
| sufficient purified water to make | 100% |
| gel-sol transition temperature | 21° C. |

EXAMPLE 3

| Gentamycin sulfate | 0.1% |
|---|---|
| Tetronic ® 1307 | 25.0% |
| Benzalkonium chloride | 0.01% |
| Sodium chloride | 0.05% |

-continued

| pH adjusted with HCl to 4 |  |
|---|---|
| sufficient purified water to make | 100% |
| gel-sol transition temperature | 26° C. |

EXAMPLE 4

| Chloramphenicol | 0.5% |
|---|---|
| Tetronic ® 1508 | 20.0% |
| Sodium acetate | 0.3% |
| Benzalkonium chloride | 0.01% |
| pH adjusted with HCl to 5 |  |
| sufficient purified water to make | 100% |
| gel-sol transition temperature | 27° C. |

EXAMPLE 5

| Lidocaine | 5.0% |
|---|---|
| Tetronic ® 1307 | 25.0% |
| Benzalkonium chloride | 0.01% |
| pH adjusted with HCl to 4 |  |
| sufficient purified water to make | 100% |
| gel-sol transition temperature | 32° C. |

EXAMPLE 6

| Sodium acetate | 2.0% |
|---|---|
| Tetronic ® 1307 | 21.0% |
| Benzalkonium chloride | 0.01% |
| pH adjusted with HCl to 5 |  |
| sufficient purified water to make | 100% |
| gel-sol transition temperature | 25° C. |

If the pharmaceutical compositions of Examples 1–6 were compared with similar compositions but without the polymer, it would be expected that the compositions of Examples 1–6 would result in greater sustained concentrations of the drug at the site of administration.

Following the procedure of Examples 1–6 one can use an appropriate amount of the polymers listed below in place of the Tetronic ® 1307 or Tetronic ® 1508 polymer used in Examples 1–6.

Tetronic 1107
Tetronic 908
Tetronic 707

Following the procedure of Examples 1–6 one can use an appropriate amount of the drugs previously enumerated in this application.

What is claimed is:

1. An aqueous pharmaceutical composition for administration to the skin comprising
   a. 10% to 50% by weight to a polyoxamine polymer of the formula

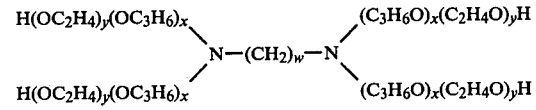

wherein w is an integer of from 2 to 6 containing approximately 40% to 80% poly(oxyethylene) and approximately 20 to 60% poly(oxypropylene) and having a molecular weight of 7,000 to 50,000; and x and y are any integers within the above contraints; and b. a pharmacologically effective amount of drug selected from the group consisting of antibacterial substances, anti-infectives, anesthetics, anti-inflammatories, anti-parasitics, antivirals, antifungals, analgesics; and diagnostics; and c. a pharmaceutically acceptable acid or base being in sufficient quantity to adjust the pH of the composition to range from 2 to 9 and wherein the composition is liquid at about room temperature or below.

2. The composition of claim 1 wherein the polymer is one wherein w is 2.

3. The composition of claim 1 wherein the polymer is Tetronic ® 1307.

4. The composition of claim 1 wherein the gel-sol transition temperature of the composition is room temperature or below and said composition is liquid at this temperature.

5. The composition of claim 1 wherein the antibacterial substances are selected from the group consisting of beta-lactam antibiotics, tetracyclines, chloramphenicol, neomycin, gramicidin, bacitracin, sulfonamides, aminoglycoside antibiotics, tobramycin, nitrofurazone, nalidixic acid and analogs, the antimicrobial combination of fludalanine/pentizidone and nitrofurazone.

6. The composition of claim 5 wherein the β-lactam antibiotics are selected from the group consisting of cefoxitin, n-formamidoyl thienamycin, and thienamycin derivatives.

7. The composition of claim 1 wherein the anti-infectives are selected from the group consisting of iodine, chloramines, benzalkonium chloride and phenol.

8. The composition of claim 1 wherein the anti-inflammatory drugs are selected from the group consisting of cortisone, hydrocortisone, betamethasone, dexamethasone, fluocortolone, prednisolone, triamcinalone, indomethacin, sulindac and its salts and corresponding sulfide.

9. A composition of claim 1 wherein the antiparasitic compound is ivermectin.

10. The composition of claim 1 wherein the antiviral effective compounds are selected from the group consisting of acyclovir and interferon.

11. A composition of claim 1 wherein the anesthetics are selected from the group consisting of benzocaine, lidocaine and dibucaine.

12. The composition of claim 1 wherein the antifungal agent is selected from the group consisting of tolnaftate, undecylenic acid, salicylic acid, zinc undecylenate and thiabendazole.

13. The composition of claim 1 wherein the analgesic drug is selected from the group consisting of methylsalicylate, menthol, camphor, methylnicotinate, triethanolamine salicylate, glycol salicylate and salicylamine.

14. The composition of claim 1 wherein the diagnostic compound is selected from the group consisting of n-alkyl carbonates, cholesteryl oleyl carbonate, cholesteryl nonanoate or cholesteryl benzoate all in proper proportions to effect liquid crystal responses.

15. The composition of claim 1 which includes a buffering agent or salt of from 0 to 5% by weight of the composition.

16. The composition of claim 15 wherein the buffering agent or salt is selected from the group consisting of alkali or alkali earth carbonates, chlorides, sulfates, phosphates, bicarbonates, citrates, borates, acetates and succinates.

17. The composition of claim 1 which includes from 0.001% to 5% weight of the composition of a preservative.

18. The composition of claim 17 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

19. The composition of claim 1 wherein the acid or base is selected from the group consisting of hydrochloric acid or sodium hydroxide.

20. A method of treating a condition requiring pharmacological treatment which comprises administering to the skin of a patient a liquid drug delivery vehicle comprising:

a. 10% to 50% by weight of a polymer of the formula $$\begin{array}{c} H(OC_2H_4)_y(OC_3H_6)_x \\ \\ H(OC_2H_4)_y(OC_3H_6)_x \end{array} N-(CH_2)_w-N \begin{array}{c} (C_3H_6O)_x(C_2H_4O)_yH \\ \\ (C_3H_6O)_x(C_2H_4O)_yH \end{array}$$

wherein w is an integer of from 2 to 6 containing approximately 40% to 80% poly(oxyethylene) and approximately 20–60% poly(oxypropylene) and having a molecular weight of 7,000 to 50,000; and x and y are any integers within the above constraints; and b. a pharmacologically effective amount of drug selected from the group consisting of antibacterial substances, anti-infectives, anesthetics, anti-inflammatories, anti-parasitics, antivirals, antifungals, analgesics; and diagnostics; and c. a pharmaceutically acceptable acid or base being in sufficient quantity to adjust the pH of the composition to range from 2 to 9 and wherein the composition is liquid at about room temperature or below.

21. A method of treatment according to claim 19 wherein the polymer is one wherein w is 2.

22. A method of treatment according to claim 20 wherein the polymer is Tetronic ® 1307.

23. A method of treatment according to claim 20 wherein the gel-sol transition temperature of the composition is room temperature or below and said composition is liquid at this temperature.

24. A method of treatment according to claim 20 wherein the mechanical properties of the skin are restored to a flexible and emollient condition.

25. A method of treatment according to claim 20 wherein the antibacterial substances are selected from the group consisting of beta-lactam antibiotics, tetracyclines, chloramphenicol, neomycin, gramicidin, bacitracin, sulfonamides, aminoglycoside antibiotics, tobramycin, nitrofurazone, nalidixic acid and analogs, the antimicrobial combination of fludalanine/pentizidone and nitrofurazone.

26. A method of treatment according to claim 25 wherein the β-lactam antibiotics are selected from the group consisting of cefoxitin, n-formamidoyl thienamycin and thienamycin derivatives.

27. The method of treatment according to claim 20 wherein the anti-infectives are selected from the group consisting of iodine, chloramines, benzalkonium chloride and phenol.

28. A method of treatment according to claim 20 wherein the anti-inflammatory drugs are selected from the group consisting of cortisone, hydrocortisone, betamethasone, dexamethasone, fluocortolone, prednisolone, triamcinalone, sulindac and its salts and corresponding sulfide.

29. A method of treatment of claim 20 wherein the antiparasitic compound is ivermectin.

30. A method of treatment according to claim 20 wherein the antiviral effective compounds are selected from the group consisting of acyclovir, idoxuridine and interferon.

31. A method of treatment according to claim 20 wherein the anesthetics are selected from the group consisting of benzocaine, lidocaine and dibucaine.

32. A method of treatment according to claim 20 wherein the antifungal agent is selected from the group consisting of tolnaftate, undecylenic acid, salicylic acid, zinc undecylenate and thiabendazole.

33. A method of treatment according to claim 20 wherein the analgesic drug is selected from the group consisting of methylsalicylate, menthol, camphor, methylnicotinate, triethanolamine salicylate, glycol salicylate and salicylamine.

34. A method of treatment according to claim 20 wherein the diagnostic compound is selected from the group consisting of cholesteryl n-alkyl carbonates, cholesteryl oleyl carbonate, cholesteryl nonanoate or cholesteryl benzoate all in proper proportions to effect a liquid crystal response.

35. A method of treatment according to claim 20 wherein the composition includes a buffering agent or salt of from 0% to 5% by weight of the composition.

36. A method of treatment according to claim 35 wherein the buffering agent or salt is selected from the group consisting of alkali or alkali earth carbonates, chlorides, sulfates, phosphates, bicarbonates, citrates, borates, acetates and succinates.

37. A method of treatment according to claim 20 wherein the composition includes from 0.001% to 5% by weight of the composition of a preservative.

38. A method of treatment according to claim 37 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

39. A method of treatment according to claim 19 wherein the acid or base is selected from the group consisting of hydrochloric acid or sodium hydroxide.

40. An aqueous pharmaceutical composition for administration to the skin of a patient as a protective covering thereof comprising:

a. 10% to 50% by weight to a polyoxamine polymer of the formula

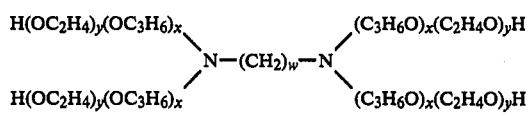

wherein w is an integer of from 2 to 6 containing approximately 40% to 80% poly(oxyethylene) and approximately 20 to 60% poly(oxypropylene) and having a molecular weight of 7,000 to 50,000; and x and y are any integers within the above constraints; and b. a pharmacologically effective amount of drug selected from the group consisting of antibacterial substances, anti-infectives, anesthetics, anti-inflammatories, anti-parasitics, antivirals, antifungals, analgesics; and diagnostics; and c. a pharmaceutically acceptable acid or base being in sufficient quantity to adjust the pH of the composition to range from 2 to 9 and wherein the composition is liquid at about room temperature or below.

41. The composition of claim 40 wherein the polymer is one where w is 2.

42. The composition of claim 40 wherein the polymer is Tetronic ® 1307.

43. The composition of claim 40 wherein the gel-sol transition temperature of the composition is room temperature or below and said composition is liquid at this temperature.

44. The composition of claim 40 which includes a buffering agent or salt of from 0 to 5% by weight of the composition.

45. The composition of claim 44 wherein the buffering agent or salt is selected from the group consisting of alkali or alkali earth carbonates, chlorides, sulfates, phosphates, bicarbonates, citrates, borates, acetates and succinates.

46. The composition of claim 40 which includes from 0.001% to 5% by weight of the composition of a preservative.

47. The composition of claim 46 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

48. The composition of claim 40 wherein the acid or base is selected from the group consisting of hydrochloric acid or sodium hydroxide.

* * * * *